(12) United States Patent
Suzuki et al.

(10) Patent No.: US 10,258,906 B2
(45) Date of Patent: Apr. 16, 2019

(54) METAL FILTER AND METHOD FOR CONCENTRATING CANCER CELLS

(71) Applicant: HITACHI CHEMICAL COMPANY, LTD., Chiyoda-ku, Tokyo (JP)

(72) Inventors: Takahiro Suzuki, Oyama (JP); Hisashige Kanbara, Oyama (JP); Yoshihito Kikuhara, Oyama (JP); Kyosuke Suzuki, Tsukuba (JP)

(73) Assignee: HITACHI CHEMICAL COMPANY, LTD., Tokyo (JP)

( * ) Notice: Subject to any disclaimer, the term of this patent is extended or adjusted under 35 U.S.C. 154(b) by 0 days.

(21) Appl. No.: 15/409,747

(22) Filed: Jan. 19, 2017

(65) Prior Publication Data

US 2017/0128858 A1    May 11, 2017

Related U.S. Application Data

(63) Continuation of application No. 14/351,152, filed as application No. PCT/JP2012/076103 on Oct. 9, 2012.

(30) Foreign Application Priority Data

Oct. 14, 2011 (JP) .................. 2011-227105

(51) Int. Cl.
| | | |
|---|---|---|
| *A61M 1/36* | (2006.01) | |
| *C25D 1/00* | (2006.01) | |
| *C25D 1/08* | (2006.01) | |
| *G03F 7/00* | (2006.01) | |
| *B01D 29/01* | (2006.01) | |
| *C25D 3/12* | (2006.01) | |

(52) U.S. Cl.
CPC .............. *B01D 29/012* (2013.01); *A61M 1/36* (2013.01); *C25D 1/00* (2013.01); *C25D 1/08* (2013.01); *G03F 7/0015* (2013.01); *A61M 2207/00* (2013.01); *C25D 3/12* (2013.01)

(58) Field of Classification Search
None
See application file for complete search history.

(56) References Cited

U.S. PATENT DOCUMENTS

| | | |
|---|---|---|
| 4,575,406 A | 3/1986 | Slafer |
| 4,772,540 A | 9/1988 | Deutsch et al. |
| 9,372,136 B2 * | 6/2016 | Kanbara ................ G01N 1/405 |
| 2002/0060904 A1 | 5/2002 | Higuchi |
| 2005/0106370 A1 | 5/2005 | Takai et al. |
| 2011/0053152 A1 | 3/2011 | Goldkorn et al. |
| 2011/0244443 A1 | 10/2011 | van Rijn et al. |

FOREIGN PATENT DOCUMENTS

| | | |
|---|---|---|
| CN | 1224565 | 7/1999 |
| EP | 0213902 | 3/1987 |
| JP | H01-279791 A | 11/1989 |
| JP | 7-51521 A | 2/1995 |
| JP | 7-331479 A | 12/1995 |
| JP | 9-217191 A | 8/1997 |
| JP | 2005-212476 A | 8/2005 |
| JP | 3786313 B2 | 3/2006 |
| JP | 2006-193825 A | 7/2006 |
| JP | 2007-70703 A | 3/2007 |
| JP | 3934723 B2 | 3/2007 |
| JP | 2011-163830 A | 8/2011 |
| JP | 2013-042689 A | 3/2013 |
| WO | 2006064741 | 6/2006 |
| WO | 2010135603 | 11/2010 |

OTHER PUBLICATIONS

RW Sheard, "Understanding Turf Management" Sports Turf Newsletter, 1991, retrieved from URL: http://archive.lib.msu.edu/tic/stnew/article/1991sep4.pdf on Feb. 2, 2018. (Year: 1991).*
"Database WPI Week 199517", Thomson Scientific, London, GB AN 1995-127462, Aug. 11, 1995, XP002772746.
Search Report of EP Patent Application No. 17171696.2 dated Aug. 16, 2017.
Siewell, G.L., et al., "The thinkjet orifice plate:A part with many functions", Hewlett-packard journal, May 1985, p. 33-p. 37.
Office Action of U.S. Appl. No. 14/351,152 dated Oct. 2, 2017.
International Preliminary Report on Patentability of Appln. No. PCT/JP2012/076103 dated Apr. 24, 2014 in English.
Database WPI Week 198951, Thomson Scientific, AN 1989-374081, Nov. 10, 1989, XP002740221.
EP Search Report of Appln. No. 12839364.2 dated Jun. 8, 2015 in English.
Office Action of counterpart CN Appl. No. 201280049165.7 dated Sep. 8, 2015.

* cited by examiner

*Primary Examiner* — Allison M Fox
(74) *Attorney, Agent, or Firm* — Fitch, Even, Tabin & Flannery, LLP

(57) ABSTRACT

A metal filter includes a plurality of through holes. An opening shape of each of the plurality of through holes is a rectangle or rounded-rectangle and a length of a short side of the rectangle or a rounded rectangle is 5 to 15 μm. A method for concentrating cancer cells using the metal filter includes separating cancer cells from blood and blood cell constituents by passing blood, red blood cells, white blood cells, and platelets through the plurality of through holes while capturing cancer cells to concentrate the cancer cells.

4 Claims, 3 Drawing Sheets

*Fig.3*
(A)
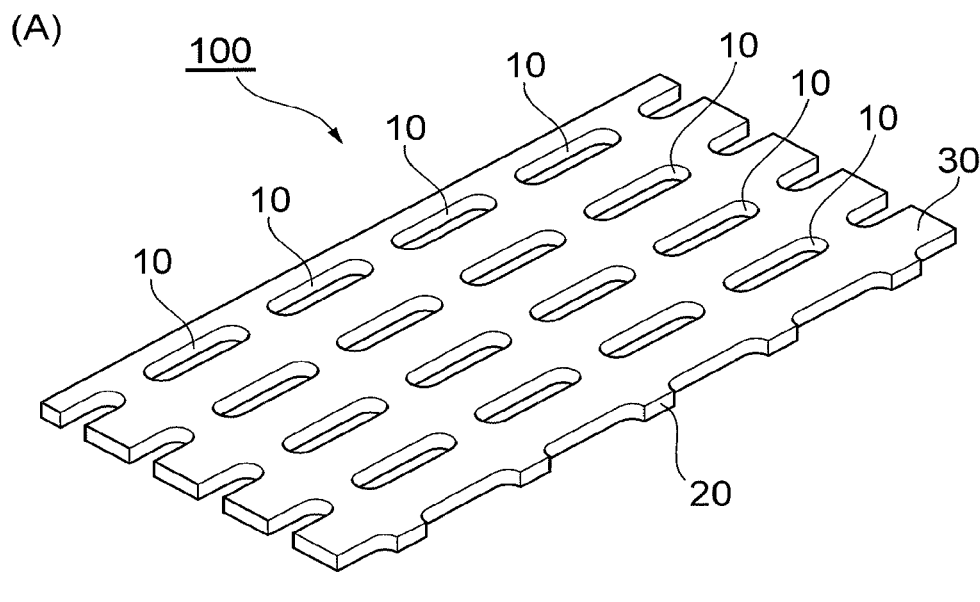
(B)
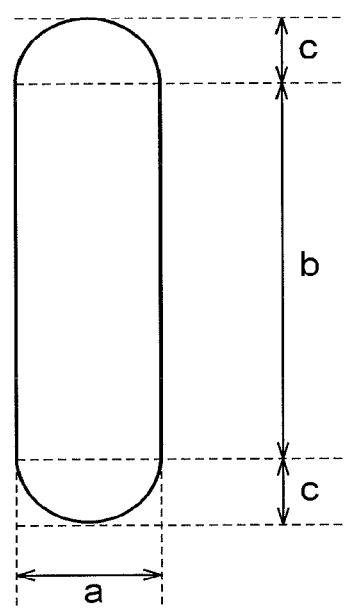

METAL FILTER AND METHOD FOR CONCENTRATING CANCER CELLS

CROSS-REFERENCE TO RELATED APPLICATION

This application is a continuation application of Ser. No. 14/351,152 filed on Apr. 11, 2014, which is a National Stage entry under 35 U.S.C. § 371 of International Application No. PCT/JP2012/076103 filed on Oct. 9, 2012, claiming priority based on Japanese Patent Application No. 2011-227105, filed on Oct. 14, 2011.

TECHNICAL FIELD

One aspect of the present invention relates to a metal filter. Another aspect of the present invention relates to a method for concentrating cancer cells using a metal filter. The present invention also relates to a method for producing a metal filter, more specifically to a method for producing a metal filter capable of efficiently capturing circulating tumor cells.

BACKGROUND ART

Cancer is one of the world nations' leading causes of death. In Japan, 300,000 or more people die of cancer every year, and its early detection and treatment are desired. Human deaths of cancer are mostly due to metastasis and recurrence of cancer. Metastasis and recurrence of cancer occur when cancer cells, which have passed through blood vessels or lymph vessels from a primary lesion, settle on and infiltrate the blood vessel wall of another organ tissue to form a minute metastasis lesion. Such cancer cells that circulate in a human body through blood vessels and lymph vessels are called circulating tumor cells (also referred to as "CTCs", hereinbelow.)

In blood, blood cell constituents such as red blood cells, white blood cells, and platelets are much included, and the number thereof is said to be 3.5 to $9 \times 10^9$ per 1 mL of blood. There exist only few CTCs among these constituents. To efficiently detect CTCs from blood cell constituents, it was necessary to separate blood cell constituents, and observation and measurement were very difficult.

Cancer cells such as CTCs are one size larger than blood cells in blood, such as red blood cells, white blood cells, or platelets. Thus, it is theoretically possible to remove these blood cell constituents using a mechanical filtering method to thereby concentrate cancer cells. Since there exist cells having a size comparable to that of CTCs among white blood cells, there is a case where it is not possible to distinguish only CTCs at high precision depending only the size difference. However, since the deformability of white blood cells is higher compared to cancer cells, white blood cells can pass through holes smaller than themselves with external forces such as suction and pressurization, and thus it becomes possible to separate white blood cells from CTCs. It is contemplated to use a metal filter as a filter to perform the mechanical filtering method.

As a method for producing a metal filter, a electroforming plating method using photolithography is known.

For example, in Patent Literature 1, a method for producing a metal mask is described, wherein, after a first photosensitive resin layer is formed on a substrate having electrical conductivity, a first photomask on which a mesh pattern is formed is overlaid on the above-described first photosensitive resin layer and exposed, development treatment is performed to remove an unnecessary portion, a first plating layer is formed on the removed portion by electroforming using the above-described substrate as one electrode such that the thickness does not exceed the above-described first photosensitive resin layer, an electrically-conductive thin film is formed on the surface of the first plating layer and the above-described first photosensitive resin layer by a sputtering method, a second photosensitive resin layer is formed on the surface of the thin film, a second photomask on which a print pattern is formed is overlaid on the above-described second photosensitive resin layer and exposed, development treatment is performed to remove an unnecessary portion, and a second plating layer is formed on the removed portion by electroforming using the above-described thin film as one electrode such that the thickness does not exceed the above-described second photosensitive resin layer, the metal mask is formed by stripping the above-described substrate and removing the exposed portion of the first photosensitive resin layer, the second photosensitive resin layer, and the thin film.

Additionally, in Patent Literature 2, a method for producing a metal mask including a step of strippably laminating or applying a photoresist on a surface of a base composed of a flat plate, a step of overlaying a pattern film on the photoresist and exposing the photoresist to a light directing straight in perpendicular to the base, a step of stripping the pattern film and transferring the photoresist to a electroforming matrix side, a step of forming a pattern resist film on the electroforming matrix by performing development and dry treatment, a step of forming electrodeposited metal on a surface not covered with the pattern resist film of the electroforming matrix, and a step of stripping the electrodeposited metal from the electroforming matrix is described.

CITATION LIST

Patent Literature

Patent Literature 1: Japanese Patent No. 3786313
Patent Literature 2: Japanese Patent No. 3934723

SUMMARY OF INVENTION

Technical Problem

However, in the production methods of Patent Literatures 1 and 2, stripping of a electroforming plating layer that is to be a metal mask is performed by manual operation (manual stripping). Thus, there were cases where damages such as wrinkles, folds, scars, and curls occurred in the metal mask.

Therefore, when a metal filter was produced by the production methods of Patent Literatures 1 and 2, there were cases where damages such as wrinkles, folds, scars, and curls occurred in the metal filter, through-holes of the metal filter were deformed, and variability occurred in the sizes of the through-holes (enlargement and reduction). It is envisaged that separation accuracy of cancer cells will be reduced if variability occurs in the sizes of the through-holes.

Accordingly, the present invention intends to provide a metal filter, a method for producing a metal filter in which damages such as wrinkles, folds, scars, and curls and deformation of fine through-holes do not occur, and a method for concentrating cancer cells using a metal filter.

Solution to Problem

The present invention provides a method for producing a metal filter comprising a lamination step of laminating a photosensitive resin composition on a copper substrate to form a photosensitive resin composition layer, an exposure step of irradiating a predetermined portion of the photosensitive resin composition layer with an active light and light-curing the exposed portion to form a cured material of the photosensitive resin composition, a development step of removing a portion other than the cured material of the photosensitive resin composition of the photosensitive resin composition layer by development to form a resist pattern composed of the cured material of the photosensitive resin composition on the copper substrate, a plating step of metal plating the resist-patterned copper substrate to form a plated layer, a dissolution step of removing the copper substrate with chemical dissolution to obtain a structure composed of the plated layer and the cured material of the photosensitive resin composition, and a stripping step of removing the cured material of the photosensitive resin composition from the structure to obtain the plated layer, wherein the plated layer is the metal filter.

According to the above-described production method of the present invention, by removing the copper substrate with chemical dissolution, it is possible to collect a plated layer to be a metal filter without depending on manual operation (manual stripping). Thus, it is possible to produce a metal filter without resulting in damages such as wrinkles, folds, scars, and curls and deformation of fine through-holes. Since there is little variability in the sizes of through-holes of a metal filter produced according to the above-described production method of the present invention, it is possible to separate and concentrate cancer cells at high separation accuracy.

When the adhesion between the substrate and the photosensitive resin composition (photoresist) is not sufficient, it is necessary to enlarge the adhesion area of the resist pattern, and thus, there is a case where it becomes difficult to produce a metal filter having fine through-holes. To form fine through-holes, it is necessary to form a resist pattern of a small adhesion area corresponding to the size of the through-hole.

In the above-described production method of the present invention, a copper substrate is used as a substrate. It is possible for copper to obtain sufficient adhesion with the photosensitive resin composition because copper is excellent in adhesion with photoresists. Therefore, according to the above-described production method of the present invention in which a copper substrate is used, it is possible to produce a metal filter having fine through-holes.

It is preferred that the above-described metal filter have a plurality of through-holes and that the opening shape of the through-hole be one or more shapes selected from the group consisting of circle, ellipse, rounded rectangle, rectangle and square. Furthermore, it is preferred that the opening shape of the through-hole include a rectangular or rounded-rectangular shape and that the length of the short side of the rectangle or rounded rectangle be 5 to 15 μm. Here, a rounded rectangle is a shape composed of two long sides of an identical length and two semicircular shapes and is a shape shown in FIG. 3(B). The length of the short side of the rounded rectangle is the length represented by "a" of FIG. 3(B). Additionally, it is preferred that the thickness of a metal filter be 3 to 50 μm.

Due to such opening shapes and sizes, cancer cells are unlikely to clog the through-holes, and it is possible to further enhance the concentration efficiency of cancer cells.

It is preferred that the thickness of the above-described plated layer be thinner than the thickness of the above-described photosensitive resin composition layer (the thickness of the cured material of the photosensitive resin composition). According to this, it is possible to securely form through-holes of the metal filter. If the thickness of the plated layer becomes thicker than the thickness of the photosensitive resin composition layer, there is a case where the plated layer connects to a portion thicker than the thickness of the cured material of the photosensitive resin composition and through-holes are not formed.

It is preferred that the above-described copper substrate be peelable copper foil. It is possible to reduce the amount of copper, to reduce the amount of chemical solubilizer and the time required to remove the copper substrate, and to enhance the productivity using peelable copper foil.

It is preferred that the above-described metal filter be a metal filter for concentration of cancer cells. The above-described metal filter has a structure particularly suitable for concentration of cancer cells. That is, the present invention also provides use of a metal filter produced by the above-described production method for concentration of cancer cells.

It is preferred that the above-described metal filter for concentration of cancer cells be a metal filter for concentration of cancer cells circulating in blood. The above-described metal filter has a structure particularly suitable for separating cancer cells circulating in the blood and blood cell constituents to concentrate cancer cells. That is, the present invention also provides use of a metal filter produced by the above-described production method for concentration of cancer cells circulating in blood.

Advantageous Effects of Invention

According to the present invention, it is possible to provide a metal filter, a method for producing a metal filter in which damages such as wrinkles, folds, scars, and curls and deformation of fine through-holes do not occur, and a method for concentrating cancer cells using a metal filter.

BRIEF DESCRIPTION OF DRAWINGS

FIG. 3(A) is a schematic view of one embodiment of the filter. FIG. 3(B) is a top view of through-holes of the filter according to one embodiment.

DESCRIPTION OF EMBODIMENTS

Figure 1:
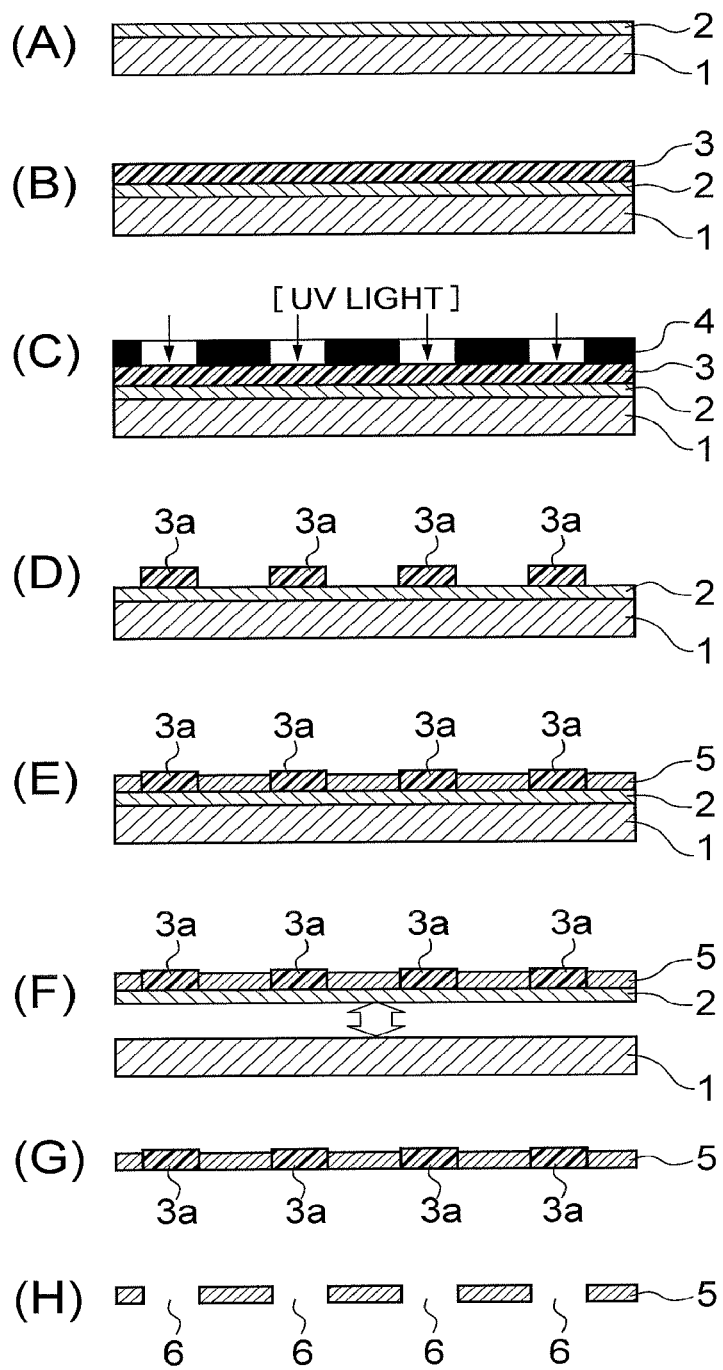
FIGS. 1(A) to (H) are flow diagrams illustrating one embodiment of the production method of the present invention.
Figure 2:
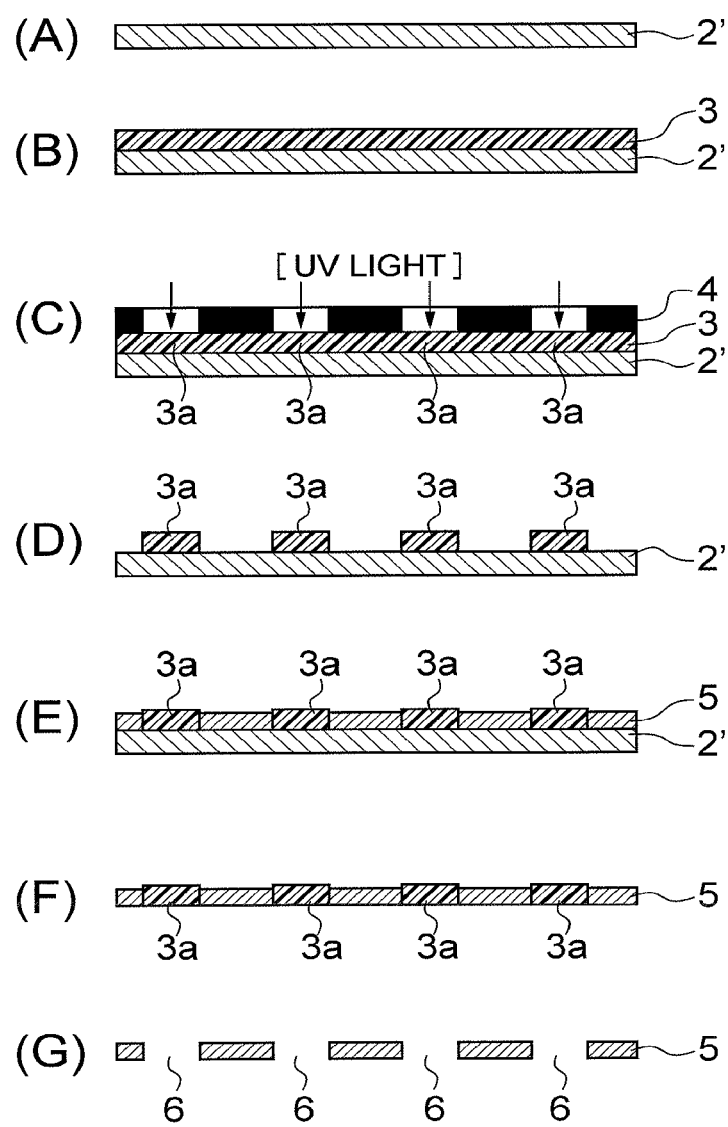
FIGS. 2(A) to (G) are flow diagrams illustrating one embodiment of the production method of the present invention.

Preferred embodiments are described hereinbelow optionally by referring to the drawings, but the present invention is not intended to be limited to these. In this context, the same reference numerals are given to the same elements, and overlapping description will be omitted in the description of the drawings. Additionally, the drawings are exaggeratedly depicted partly to facilitate understanding, and the dimensional ratios do not necessarily correspond to those of the explanation.

The method for producing a metal filter according to the embodiment comprises a lamination step of laminating a photosensitive resin composition on a copper substrate to form a photosensitive resin composition layer, an exposure step of irradiating a predetermined portion of the photosensitive resin composition layer with an active light and light-curing the exposed portion to form a cured material of the photosensitive resin composition, a development step of removing a portion other than the cured material of the photosensitive resin composition of the photosensitive resin composition layer by development to form a resist pattern composed of the cured material of the photosensitive resin composition on the copper substrate, a plating step of metal plating the resist-patterned copper substrate to form a plated layer, a dissolution step of removing the copper substrate with chemical dissolution to obtain a structure composed of the plated layer and the cured material of the photosensitive resin composition, and a stripping step of removing the cured material of the photosensitive resin composition from the structure to obtain the plated layer, and the plated layer is the metal filter.

FIGS. 1(A) to (H) are flow diagrams illustrating one embodiment of the production method of the present invention. In this embodiment, peelable copper foil is used as the copper substrate.

FIG. 1(A) shows peelable copper foil composed of a carrier layer 1 and a copper foil layer 2. In a lamination step shown in FIG. 1(B), a photosensitive resin composition is laminated on the copper foil layer 2 to form a photosensitive resin composition layer 3. Subsequently, in an exposure step shown in FIG. 1(C), the photosensitive resin composition layer 3 is irradiated with an active light (UV light) through a photomask 4 and the exposed portion is light-cured to form a cured material of the photosensitive resin composition 3a. Subsequently, in a development step shown in FIG. 1(D), a portion other than the cured material of the photosensitive resin composition 3a of the photosensitive resin composition layer 3 is removed to form a resist pattern composed of the cured material of the photosensitive resin composition 3a. Subsequently, in a plating step shown in FIG. 1(E), a plated layer 5 is formed on a copper foil layer 2 on which the resist pattern composed of the cured material of the photosensitive resin composition 3a is formed. Subsequently, as shown in FIG. 1(F), the copper foil layer 2 and the carrier layer 1 of the peelable copper foil are stripped. Subsequently, in the dissolution step shown in FIG. 1(G), the copper foil layer 2 is removed with chemical dissolution. Consequently, the cured material of the photosensitive resin composition 3a and the plated layer 5 are left. Subsequently, in the stripping step shown in FIG. 1(H), the resist pattern composed of the cured material of the photosensitive resin composition 3a is removed, and a metal filter composed of the plated layer 5 is collected. In the metal filter, through-holes 6 are formed.

FIGS. 2(A) to (G) are flow diagrams illustrating one embodiment of the production method of the present invention. In the present embodiment, a copper substrate 2' is used instead of the peelable copper foil of the above-described embodiment. The production method of the present embodiment is the same as the above-described embodiment, except that the step of stripping the copper foil layer 2 and the carrier layer 1 of the peelable copper foil shown in FIG. 1(F) does not exist. However, the copper substrate 2' is thicker than the copper foil layer 2 of the above-described embodiment, so that the chemical solubilizer and time are to be required much more in a step of removing the copper substrate 2' with chemical dissolution in the dissolution step, compared to the above-described embodiment.

Then, the method for producing the metal filter according to the embodiment will be described in more detail.

(Lamination Step)

First, the lamination step will be described. Examples of the copper substrates are not particularly limited, as long as the substrates are copper or have copper on the surface, and include copper foils with a thickness of 1 to 100 μm, copper foil tapes, and peelable copper foil. From a viewpoint of workability, peelable copper foil is preferred. Peelable copper foil is copper foil composed of at least of two layers, a very thin copper foil and a carrier layer.

As the photosensitive resin composition, either of the positive or negative type can be used, but a negative-type photosensitive resin composition is preferred. It is preferred that the negative-type photosensitive resin composition be one that contains at least a binder resin, a photopolymerizable compound having unsaturated bonds, and a photopolymerization initiator. Additionally, in the case where a positive-type photosensitive resin composition is used, since the solubility of the portion exposed to irradiation of an active light in a developer is increased, the exposed portion in the photosensitive resin composition layer is to be removed in the development step. Hereinbelow, a case where a negative-type photosensitive resin composition is used is described.

The thickness of a metal filter to be produced is to be smaller than the thickness of the photosensitive resin composition layer. Thus, it is necessary to form a photosensitive resin composition layer of a film thickness suitable for an intended thickness of the metal filter. For example, in the case where a metal filter of a thickness of 15 μm or less is produced, it is preferred to use photosensitive resin composition of a film thickness of 15 μm. Additionally, in the case where a metal filter of a thickness of more than 15 μm to 25 μm or less is produced, it is preferred to use a photosensitive resin composition of a film thickness of 25 μm. Additionally, it is preferred to use a photosensitive resin composition in which the film thickness is thin such that the hole diameter of the through-hole becomes smaller.

From a photosensitive sheet element composed of a support film, a photosensitive resin composition, and a protection film, the protection film is removed, and then, lamination of the photosensitive resin composition to the copper substrate is performed by compression-bonding the photosensitive resin composition layer of the photosensitive element to the copper substrate with heating. Thereby, a lamination composed of a copper substrate, a photosensitive resin composition layer, and support film that are laminated in sequence is obtained.

It is preferred that this lamination operation be performed under reduced pressure from the viewpoint of adhesion and conformability. The conditions such as heating temperatures and pressures for the photosensitive resin composition layer and/or the copper substrate at compression bonding are not particularly limited, but it is preferred to perform compression bonding at temperature of 70 to 130° C., and it is preferred to perform compression bonding under a pressure of about 100 to 1000 kPa. In this context, in compression-bonding of a photosensitive resin composition layer, copper substrate may be subjected to preheating treatment in order to enhance the laminatability.

(Exposure Step)

Subsequently, the exposure step will be described. The predetermined portion of the photosensitive resin composition layer on the copper substrate is irradiated with an active light, and the exposed portion is light-cured to form a cured material of the photosensitive resin composition. On this occasion, in the case where the support film existing on the photosensitive resin composition layer has transparency to the active light, it is possible to perform irradiation with the active light through the support film. In the case where the support film has light shieldability to the active light, the photosensitive resin composition layer is irradiated with the active light after the support film is removed.

Examples of the exposure method include a method for irradiating an image through a negative or positive mask pattern called art work with an active light (mask exposure method). Additionally, a method for irradiation with active light images by direct imaging exposure, such as the Laser Direct Imaging (LDI) exposure and the Digital Light Processing (DLP) exposure may be employed.

As the light source for active light, it is possible to use the known light sources. For example, those that emit ultraviolet and visible light, such as carbon arc lamps, mercury vapor arc lamps, high pressure mercury lamps, xenon lamps, gas lasers such as argon laser, solid lasers such as YAG laser, and semiconductor lasers are employed.

It is preferred that the wavelength of an active light (exposure wavelength) be in a range of 350 to 410 nm, and it is more preferred that the wavelength be in a range of 390 to 410 nm.

(Development Step)

Subsequently, the development step will be described. By removing a portion other than the cured material of the photosensitive resin composition of photosensitive resin composition layer from the copper substrate, a resist pattern composed of the cured material of the photosensitive resin composition is formed on the copper substrate. When the support film exists on the photosensitive resin composition layer, removal (development) of the portion other than the cured material of the above-described photosensitive resin composition is performed after the support film is removed. Examples of the development method include wet development and dry development, and the wet development is widely used.

In the case according to the wet development, development is performed using a developer compatible to the photosensitive resin composition in accordance with the known development method. Examples of the development method include methods using a dip system, battle system, spray system, brushing, slapping, scrapping, and shaking immersion. In the viewpoint of enhancing the resolution, the high-pressure spray system is the most suitable. These can be developed by combining two or more methods.

Examples of the developer include alkaline aqueous solutions, water-based developers, and organic solvent-based developers. The alkaline aqueous solutions, when used as a developer, are safe and stable, and its operability is excellent. Examples of the base of alkaline aqueous solutions include alkali metal hydroxides, such as hydroxides of lithium, sodium, and potassium; carbonates and bicarbonates of lithium, sodium, potassium, and ammonium; alkali metal phosphates, such as potassium phosphate and sodium phosphate; and alkali metal pyrophosphates, such as sodium pyrophosphate and potassium pyrophosphate.

As the alkaline aqueous solutions, dilute solutions, such as a 0.1 to 5% by mass sodium carbonate dilute solution, a 0.1 to 5% by mass potassium carbonate dilute solution, a 0.1 to 5% by mass sodium hydroxide dilute solution, and a 0.1 to 5% by mass sodium tetraborate dilute solution are preferred. It is preferred that the pH of the alkaline aqueous solution be in a range of 9 to 11, and the temperature is adjusted in accordance with the alkaline developability of the photosensitive resin composition layer. Into the alkaline aqueous solution, surfactants, defoaming agents, a small amount of organic solvents and the like to enhance development may be mixed.

After the portion other than the cured material of the photosensitive resin composition is removed by development to form a resist pattern composed of the cured material of the photosensitive resin composition on the copper substrate, the resist pattern may be further cured by performing heating at about 60 to 250° C. or exposure at 0.2 to 10 J/cm$^2$ as required.

(Plating Step)

Subsequently, the plating step will be described. After the development step, plating is performed on the copper substrate to form a plated layer. Examples of the plating method include solder plating, nickel plating, and gold plating. This plated layer will be the metal filter in the end.

Examples of materials for the metal filter include, but not limited to, noble metals, such as gold and silver, base metals, such as aluminum, tungsten, nickel, and chrome, and alloys of these metals. The metal may be used alone, or may be used as alloys with other metals or metal oxides to impart functionalities. Of these, it is preferred that nickel and metals including nickel as the main constituent be used because they prevent occurrence of corrosion and the like and are excellent in processability and in the aspect of cost. The main constituent herein refers to a constituent accounting for 50% by weight or more of the material.

(Dissolution Step)

Subsequently, the dissolution step will be described. After the plated layer is formed, the copper substrate is chemically dissolved and removed. Thereby, it is possible to collect a structure composed of the plated layer and the cured material of the photosensitive resin composition, which is to be a metal filter, without depending on manual operation (manual stripping). Thus, it is possible to produce a metal filter without resulting in damages such as wrinkles, folds, scars, and curls and deformation of fine through-holes. As the chemical solubilizer to dissolve the copper substrate, it is possible to use MECBRITE SF-5420B (product name, produced by MEC COMPANY LTD.), Copper selective etchant, CSS (NIHON KAGAKU SANGYO CO., LTD.) and the like.

(Stripping Step)

Subsequently, the stripping step will be described. After the dissolution step, the resist pattern is stripped with, for example, a stronger alkaline aqueous solution than the alkaline aqueous solution used for development. As this strong alkaline aqueous solution, it is preferred to use, for example, a 1 to 10% by mass sodium hydroxide aqueous solution or potassium hydroxide aqueous solution, and it is more preferred to use a 1 to 5% by mass sodium hydroxide aqueous solution or potassium hydroxide aqueous solution. By stripping the resist pattern (the cured material of the photosensitive resin composition), it is possible to collect only the plated layer alone. This plated layer is the metal filter.

Examples of the method for stripping the resist pattern include an immersion system, spray system, and system for using ultrasound, and each of these may be used alone or in combination.

(Metal Filter)

Subsequently, the shape of the metal filter is described. Examples of the opening shape of a through-hole opening of the metal filter include circle, ellipse, rounded rectangle, rectangle, square, polygon, and the like. From a viewpoint of being able to efficiently capture cancer cells, circle, rectangle, or rounded rectangle is preferred. Alternatively, from a viewpoint of preventing the metal filter from clogging, rectangle or rounded rectangle is particularly preferred.

The hole diameter of the through-hole is set depending on the size of cancer cells that are subjects to be captured. A hole diameter of a shape other than circle, such as ellipse, rectangle, and polygon means herein the maximum value of the diameter of a sphere that can pass each through-hole. The hole diameter of a through-hole will be, for example, in the case where the opening shape is rectangle, the length of the short side of the rectangle, and in the case where the opening shape is polygon, the diameter of an inscribed circle of the polygon. In the case where the opening shape is rectangle or rounded rectangle, even if the constituents that are the subjects to be captured are in the state of being captured in the through-holes, a gap will be made in the opening in the direction of the long side of the opening shape. Since it is possible for liquid to pass through this gap, it is possible to prevent clogging of the filter.

It is preferred that the average opening ratio of the through-holes of the metal filter be 0.1 to 50%, it is more preferred that the ratio be 0.5 to 40%, it is further more preferred that the ratio be 1 to 30%, and it is most preferred that the ratio be 1 to 10%. Here, an opening ratio refers to an area occupied by through-holes against the area of the corresponding region in the predetermined area on the filter. An average opening ratio refers to an area occupied by through-holes against the area of the whole filter. If the average opening ratio is 0.1 to 50%, it is possible to sufficiently secure the strength of a filter, and processing is easy. Additionally, it is possible to prevent clogging of the filter from occurring and to secure the concentration performance of the filter.

It is preferred that the thickness of a metal filter be 3 to 50 μm, it is more preferred that the thickness be 5 to 40 μm, and it is particularly preferred that the thickness be 5 to 30 μm. If the film thickness of a filter is 3 to 50 μm, the strength of the filter is secured, and the handling of the filter is excellent. Additionally, the productivity of the filter is excellent. The filter is not to be disadvantageous in cost due to excessive consumption of materials, and is easy to micromachine.

FIG. 3(A) is a schematic view showing one embodiment of a metal filter that can be produced according to the production method of the present invention. The metal filter 100 is composed of a substrate (plated layer) 20 in which a plurality of through-holes are formed. The opening shape of the through-holes 10 is a rounded rectangle. The arrangement of the through-holes 10 may be an aligned arrangement as in FIG. 1(A), may be a staggered arrangement in which the arrangement is misaligned in each column, and may be a random arrangement in which the through-holes are arbitrarily arranged.

FIG. 3(B) is a top view of the through-holes 10 of the metal filter according to the above-described embodiment. The opening shape of the through-holes 10 is a rounded rectangle, which is a shape in which two semicircular shapes having a radius of "c" is connected adjacent to short sides of a rectangle in which the short side is "a" and the long side is "b". In one embodiment, "a", "b", and "c" are respectively 8, 22, and 4 μm.

EXAMPLES

Hereinafter, examples of the present invention are illustrated, and the present invention is more specifically described, but the present invention is not limited to these examples, and various modifications are possible to the extent that the modifications do not depart from the technical spirit of the invention.

Example 1

A photosensitive element (PHOTEC RD-1225: thickness 25 μm, produced by Hitachi Chemical Company, Ltd.) is compression-bonded on a copper foil layer of a 250 mm square substrate (a substrate in which peelable copper foil t 18 μm is bonded with the surface of MCL-E679F t 0.5× 250×250 N3DB: (MCL-E679F t 0.5×250×250 18D), produced by Hitachi Chemical Company, Ltd.) to form a photosensitive resin composition layer. Compression bonding was performed under conditions of a roll temperature of 90° C., a pressure of 0.3 MPa, and a conveyor speed of 2.0 m/minute.

Then, a glass photomask is placed gently on the above-described photosensitive resin composition layer. The photomask is of a shape in which the shape of a light transmission portion is a rounded rectangle, and these rounded rectangles are aligned in a pitch of 60 μm in both the long and short axial directions facing the same direction. Additionally, as for the size of the rounded rectangle, "a", "b", and "C" of FIG. 3(B) are respectively 8 μm, 22 μm, and 4 μm. Subsequently, under vacuum of 80 kPa or less, the above-described photomask was irradiated from the upper side with an ultraviolet radiation of a light exposure of 30 mJ/cm$^2$ via an ultraviolet irradiation apparatus.

Then, development was performed with a 1.0% sodium carbonate aqueous solution, and a resist pattern composed of a cured material of the photosensitive resin composition was formed on the copper substrate. This resist-patterned copper substrate was immersed in a nickel plating liquid adjusted to pH 4.5 and plated at a temperature of 55° C. for about 20 minutes. The composition of the nickel plating liquid is shown in Table 1.

TABLE 1

| Plating liquid composition | Concentration (g/L) |
| --- | --- |
| Nickel sulfamate | 450 |
| Nickel chloride | 5 |
| Boric acid | 30 |

Then, the copper foil layer on which the nickel-plated layer had been formed was stripped from the peelable copper foil carrier. Subsequently, the copper foil layer on which the nickel-plated layer had been formed was immersed in a chemical solubilizer (MECBRITE SF-5420B, produced by MEC COMPANY LTD.) and stirred at 40° C. for about 120 minutes to dissolve and remove the copper foil layer. Thereby, a structure composed of the plated layer and the cured material of the photosensitive resin composition was collected.

Finally, the collected structure was immersed in a resist stripping liquid (P3 Poleve, produced by Henkel) and ultrasonically treated at 60° C. for about 40 minutes to remove the cured material of the photosensitive resin composition.

According to the operations hereinabove, a metal filter of Example 1 in which there were no damages such as wrinkles, folds, scars, and curls and which had through-holes of sufficient accuracy was prepared.

Example 2

A metal filter of Example 2 was prepared as in Example 1, except that the shape of a light transmission portion of the photomask was changed to a rounded rectangle in which "a", "b" and "c" of FIG. 3(B) are respectively 5 μm, 15 μm, and 2.5 μm.

Example 3

A metal filter of Example 3 was prepared as in Example 1, except that the shape of a light transmission portion of the photomask was changed to a circle of a diameter of 5 µm.

Example 4

A metal filter of Example 4 was prepared as in Example 1, except that the time for nickel plating was changed to about 3 minutes. The film thickness of the metal filter, as a result of measurement with a film thickness gauge (Digimatic Indicator ID-C112C, produced by Mitutoyo Corporation) by holding the filter between the contact point and the base, was 3 µm.

Comparative Example 1

A metal filter of Comparative Example 1 was prepared as in Example 1, except that the copper substrate was replaced with a stainless plate (SUS304, finishing ¾H, thickness 100 µm, produced by Nisshin Steel Co., Ltd.) and that stripping of the filter from the substrate was performed manually instead of chemical dissolution and removal with a chemical liquid.

Consequently, damages such as wrinkles, folds, scars, and curls occurred, and variability in the sizes (enlargement and reduction) due to deformation of the through-holes occurred. Particularly, occurrence of curls was severe and was at the level in which the filter could not be used as a filter.

Additionally, in the metal filter of Comparative Example 1, resist falling and dropout occurred due to insufficient adhesion between the cured material of the photosensitive resin composition and the stainless plate after the resist pattern was formed. Because of this, deformation and array distortion of the through-holes occurred.

Experiment Example 1

Glass beads (High-precision Unibeads SPM-16: particle size 16±2 µm, barium titanate glass, produced by UNION CO., LTD.) was mixed with physiologic saline, and a filtration experiment of the metal filter of Example 1 was performed. The glass beads were used instead of cancer cells.

The metal filter of Example 1 was set in a filter holder (Swinnex 13, produced by MILLIPORE), and a mixed solution of physiologic saline and the glass beads was injected with a syringe and filtered. As a result of confirmation of the surface of the metal filter after filtration with an optical microscope, the glass beads of a particle size of about 16 µm did not pass through holes of a short side of 8 µm, and were left on the filter surface in a state where the beads clogged the holes. The result in which the number of glass beads supplemented was counted against the number of glass beads charged is shown in Table 2. It was confirmed that the metal filter of Example 1 has sufficient ability to capture glass beads. From this result, it is expected that sufficient capturing ability will be exhibited also when cancer cells are used.

TABLE 2

|  | Number of glass beads charged | Number of glass beads supplemented | Supplement ratio |
| --- | --- | --- | --- |
| First time | 29 pieces | 29 pieces | 100% |
| Second time | 32 pieces | 32 pieces | 100% |
| Total | 61 pieces | 61 pieces | 100% |

REFERENCE SIGNS LIST

1 Carrier layer, 2 Copper foil layer, 2' Copper plate, 3 Photosensitive resin composition layer, 3a Cured material of photosensitive resin composition, 4 Photomask, 5 Plated layer, 6, 10 Through-holes, 20 Substrate (plated layer), 100 Filter, a Short side, b Long side, c Radius

The invention claimed is:

1. A method for concentrating cancer cells, comprising:
providing a metal filter having a plurality of through holes, wherein an opening shape of each of the plurality of through holes is a rectangle or rounded-rectangle and a length of a short side of the rectangle or a rounded rectangle is 5 to 15 µm, the through holes have an average aperture ratio of 1% to 10%, and the metal filter comprises a metal selected from the group consisting of gold, silver, aluminum, tungsten, nickel, chrome, and an alloy of two or more of these metals, as a main constituent; and
separating cancer cells from blood and blood cell constituents by passing blood, red blood cells, white blood cells, and platelets through the plurality of through holes while capturing cancer cells to concentrate the cancer cells.

2. The method for concentrating cancer cells according to claim 1, wherein the thickness of the metal filter is 3 to 50 µm.

3. The method for concentrating cancer cells according to claim 1, wherein an opening shape of each of the plurality of through holes is a rectangle.

4. The method for concentrating cancel cancer cells according claim 1, wherein an opening shape of each of the plurality of through holes is a rounded-rectangle.

* * * * *